US005759406A

United States Patent [19]

Phelps et al.

[11] Patent Number: 5,759,406
[45] Date of Patent: Jun. 2, 1998

[54] ADSORPTION PROCESS FOR ORGANIC BASE RECOVERY FROM AQUEOUS BRINE SOLUTIONS

[75] Inventors: Peter David Phelps, Schenectady; Joseph John Caringi, Niskayuna, both of N.Y.; Larry Ivis Flowers, Evansville, Ind.; Eugene Pauling Boden, Scotia, N.Y.; David Lee Ramsey, Mt. Vernon, Ind.

[73] Assignee: General Electric Company, Schenectady, N.Y.

[21] Appl. No.: 911,754

[22] Filed: Aug. 15, 1997

Related U.S. Application Data

[63] Continuation of Ser. No. 641,971, May 1, 1996, abandoned, which is a continuation-in-part of Ser. No. 291,635, Aug. 17, 1994, abandoned.

[51] Int. Cl.$^6$ ................................................ B01D 15/00
[52] U.S. Cl. .................................... 210/673; 210/692
[58] Field of Search ........................... 210/670, 673, 210/692, 903, 908

[56] References Cited

U.S. PATENT DOCUMENTS

| 3,531,463 | 9/1970 | Gustafson | 210/692 |
| 4,297,220 | 10/1981 | Meitzner et al. | 210/690 |
| 4,415,456 | 11/1983 | Chandler, Jr. | 210/674 |
| 4,729,834 | 3/1988 | Itoh et al. | 210/670 |
| 5,087,671 | 2/1992 | Leoppky et al. | 210/692 |

*Primary Examiner*—Ivars Cintins
*Attorney, Agent, or Firm*—William H. Pittman

[57] ABSTRACT

An adsorption process uses a non-ion-exchangeable adsorbent polymeric resin of a monoethylenically unsaturated monomer such as styrene and a polyvinylidene monomer such as divinylbenzene for the adsorption of organic bases, such amines, amine salts and guanidinium salts, from high ionic strength aqueous solutions. Desorption may be employed for the recovery of said organic bases, and said adsorbent resin may be regenerated.

9 Claims, No Drawings

ADSORPTION PROCESS FOR ORGANIC BASE RECOVERY FROM AQUEOUS BRINE SOLUTIONS

CROSS-REFERENCE TO RELATED APPLICATION

This application is a continuation of application Ser. No. 08/641,971, filed May 1, 1996, now abandoned, which is a continuation-in-part of application Ser. No. 08/291,635 filed Aug. 17, 1994, now abandoned.

BACKGROUND OF THE INVENTION

The present invention relates to a process for the recovery of amines, amine salts, guanidines, guanidinium salts, or mixtures thereof from aqueous brine solutions. More particularly the present invention relates to a process for the recovery of such compounds from by-product aqueous brine solutions resulting from the interfacial condensation polymerization of bisphenols and phosgene to form polycarbonates, or from the displacement reaction of bisphenol salts with various phthalimides.

In the practice of interfacial polymerization to produce polycarbonates, a mixture of bisphenol and a phenolic chain-stopper is phosgenated under interfacial reaction conditions in the presence of an organic solvent, and in the presence of an effective amount of a catalyst which may be an organic amine or amine salt or mixture thereof. The bisphenol is present as an alkali metal salt in an aqueous phase which is catalytically phosgenated by a suitable catalyst dissolved in an organic phase along with the phosgene. Suitable organic solvents include chlorinated aliphatic hydrocarbons, such as methylene chloride, chloroform, carbon tetrachloride, dichloroethane, trichloroethane, tetrachloroethane, dichloropropane and 1,2-dichloroethylene; substituted aromatic hydrocarbons such as, chlorobenzene, o-dichlorobenzene, and the various chlorotoluenes. The chlorinated aliphatic hydrocarbons, especially methylene chloride, are preferred.

An effective amount of phase transfer catalyst for these reactions is from 0.05 to 10.00 mole % based on the moles of bisphenol or salt thereof in the reaction mixture. A preferred range of the phase transfer catalyst ranges from about 0.1 to about 0.7 mole %. When a co-catalyst is used, the quantity of co-catalyst ranges from about 0.001 to about 1.0 mole % based on the moles of bisphenol charged to the mixture.

Sufficient alkali metal hydroxide can be utilized to raise the pH of the polycarbonate reaction mixture to 10.5 prior to phosgenation to cause dissolution of some of the bisphenol and chain-stopper into the aqueous phase. Aqueous alkali or alkaline earth metal hydroxide can be used to maintain the pH of the phosgenation mixture which can be in the range of between about 7 to about 12.5 and preferably 10 to 12. Some of the alkali metal and alkaline earth metal hydroxides which can be employed are sodium hydroxide, potassium hydroxide and calcium hydroxide. Sodium and potassium hydroxides and particularly sodium hydroxide is preferred.

Phosgenation of the bisphenol can be conducted in a wide variety of either batch or continuous reactors. Such reactors are, for example, stirred tank reactors, which may be either batch or continuous flow. Additional reactors which are included are agitated column and recirculating loop continuous reactors.

The volume ratio of aqueous to organic phase during and at the termination of the phosgenation reaction can be in the range of 0.2–1.1. Reaction temperature can be in the range of between about 15°–50° C. When the preferred organic liquid is utilized, such as methylene chloride, the reaction may be conducted at reflux which can be 35°–42° C. The reaction can be conducted at atmospheric pressures, although sub- or super-atmospheric pressures may be employed if desired.

During phosgenation, the mixture is agitated, such as, by using a stirrer or other conventional equipment. The phosgenation rate can vary from between about 0.02–0.2 mole of phosgene, per mole of bisphenol per minute.

Depending upon the molecular weight of polycarbonate desired, phenolic chain-stoppers can be used in a proportion of from 1–8 mole percent based on the total moles of bisphenol. Some of the phenolic chain-stoppers are, phenol, t-butylphenol, p-cumylphenol and the chloroformates of these phenols.

The aqueous phase in the polycarbonate-forming reaction contains alkali metal salts resulting from both the pH control of the reaction and the reaction products of the alkali metal salt of the bisphenol as well as water soluble chloroformate hydrolysis products. Thus, this aqueous phase may be characterized as a brine, typically having a fairly high ionic strength, usually at least 10% (by weight) sodium chloride.

The amines, amine salts or mixtures thereof used as catalysts in the interfacial condensation polymerization may be soluble in both the aqueous and the organic phases. Thus while the organic phase may be conveniently recycled after recovery of the polycarbonate polymer, it may be depleted in the concentration of the catalyst or catalyst mixture. That is, the catalysts used have a finite solubility in both liquid phases. Consequently as the process proceeds the amine or amine salt catalysts dissolve out of the organic phase and into the brine phase. This results in an undesirable loss of an expensive catalytic component. Further, the presence of the amine or amine salt catalyst may render the brine unsuitable for many other uses even including simple dilution and disposal until the amine or amine salt has been extracted from the brine by some suitable process; heretofore typically either an energy-intensive extractive steam distillation or a liquid-liquid extraction.

One step in the preparation of polyetherimides is an anhydrous displacement reaction between an alkali metal salt of a dihydroxyaromatic compound and a monomeric or polymeric nitro- or halo-substituted aromatic compound, typically a mono- or bisphthalimide, in an organic system employing toluene or the like as the organic solvent. Suitable organic solvents include toluene and chlorobenzene. In similar fashion to the polycarbonate-forming reaction, a phase transfer catalyst, typically a quaternary ammonium halide or hexasubstituted guanidinium halide, is usually employed. Further processing, which includes a step of washing with an aqueous alkali solution, results in the formation as a by-product of an aqueous brine containing the phase transfer catalyst and a relatively high concentration of at least one salt such as sodium chloride, sodium bromide or sodium nitrite.

U.S. Pat. No. 4,297,220 describes the preparation of various suspension polymers, including styrene polymers crosslinked with divinylbenzene, and briefly suggests their use as "absorbents for organic fluids". U.S. Pat. No. 4,729,834 compares such polymers adversely with certain crosslinked (meth)acrylamides as adsorbents for organic compounds. Neither of these patents deals with the removal of organic bases from brine solutions of high concentration. Moreover, in U.S. Pat. No. 4,729,834 it is considered important to use a temperature gradient so that adsorption takes place at a higher temperature than desorption.

It is therefore desirable to provide a means of removing amines, substituted guanidines, salts thereof and their mixtures from brine solutions. It is also desirable to be able to recover the catalytic species therein in a fashion that would permit their recycle and re-use as catalysts.

SUMMARY OF THE INVENTION

There is provided in the present invention a method for the recovery of compounds selected from the group consisting of nitrogen and phosphorus bases and their salts (hereinafter sometimes collectively "organic bases") from aqueous solutions having a high ionic strength by adsorbing said compounds onto an adsorbent resin. The brine is thereby purified of said compounds. The adsorbed compounds are washed from the resin by means of another aqueous solution. More particularly there is provided in the present invention a process for the recovery and recycle of such compounds or mixtures thereof as phase transfer catalysts used in the interfacial condensation polymerization to produce polycarbonates, and/or in the displacement reaction of bisphenol salts with imides to produce monomeric or polymeric ether imides.

In one of its aspects, the invention is a process for the adsorption of organic bases from an aqueous solution having an ionic strength equivalent to a sodium chloride level of about 5–40% by weight and having therein one or more of said organic bases, comprising contacting said aqueous solution with a non-ion-exchangeable adsorbent polymeric resin whereby said solution is depleted in the concentration of said organic bases by the adsorption thereof onto said resin.

Another aspect is a process for the desorption of organic bases adsorbed onto an adsorbent polymeric resin, comprising washing said resin with an effective amount of a solvent effective to remove said organic bases therefrom, whereby said organic bases are dissolved in said solvent.

Still another aspect is a process which includes both the adsorption and desorption steps described hereinabove.

DETAILED DESCRIPTION

Preferred Embodiments

Preferably the process of the present invention is utilized for the adsorption, desorption and recovery of one or more amines, amine salts, substituted guanidines, substituted guanidinium salts or mixtures thereof. More preferably, the present invention is utilized for the adsorption, desorption, and recovery of one or more of said organic bases present either singly or as a mixture. Most preferably, the present invention is utilized for the adsorption, desorption, and recovery thereof.

The term "amine salt" refers to the ionic salts of primary, secondary, tertiary and quaternary ammonium ions, and these compounds as well as guanidinium salts are nitrogen compounds. The preferred compounds recoverable by the process of the present invention are tertiary and quaternary ammonium and hexasubstituted guanidinium salts. These preferences arise naturally from the selection of catalysts and co-catalysts employed in the aforementioned reactions. Thus depending on the particular starting materials and products desired and such conditions as kinetics, solubility, steric factors and degree of polymerization, different catalyst systems will be employed. Under varying circumstances, one catalyst system may be preferred over another.

The catalysts employed in these reactions present process management difficulties which the present invention alleviates. High molecular weight amines and their salts have a tendency to function as surfactants in addition to fulfilling a catalytic role in the process, hindering, for example, the break-up of a polymerization emulsion; thus their continued presence is generally not preferred. When low molecular weight amine or amine salts are used as catalysts, the high solubility of the resulting organic ammonium salts renders most materials ineffective for separating the ammonium compounds from the water solvent, aggravating losses. By providing a means for recovering such amines or amine salts, the preferred lower molecular weight amine or amine salt phase transfer catalysts or co-catalysts may be more advantageously employed because losses due to aqueous solubility are minimized.

Some salts useful as phase transfer catalysts or co-catalysts are

and

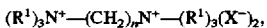

wherein each $R^1$ is independently $C_{1-10}$ alkyl, Q is nitrogen or phosphorus, X is halogen or $-OR^2$ and $R^2$ is H, $C_{1-8}$ alkyl or $C_{6-18}$ aryl. Tertiary amines such as triethylamine also function as catalysts. These organic amines and phosphines, salts thereof and the like are amenable to recovery from brine solutions by the process of the present invention.

Guanidinium salts which are similarly amenable include the hexasubstituted compounds having the formula

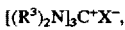

wherein $R^3$ is a $C_{1-6}$ primary alkyl radical or two $R^3$ values with the connecting nitrogen atom form a saturated heterocyclic radical. Such compounds may be prepared by a three-step method from a secondary amine having the formula $(R^3)_2NH$. The first step is the phosgenation of said secondary amine to produce a tetrasubstituted urea; the second is the further phosgenation of the tetrasubstituted urea to form a chloroformamidinium chloride, also known as a "Vilsmeier salt"; and the third is the reaction of the Vilsmeier salt with further secondary amine to produce the hexasubstituted guanidinium chloride.

The process of the invention preferably utilizes non-ionic resins that heretofore have been disclosed as suitable adsorbents for organic fluids as taught in the aforementioned U.S. Pat. No. 4,297,220 herein incorporated by reference. In contrast to the separation processes taught in said patent wherein organic fluids are separated one from the other, the present invention is a process wherein organic bases are selectively adsorbed from aqueous media on a resin that contains no ion exchange sites. More particularly, the present invention provides a process wherein the organic bases are adsorbed from an aqueous medium having a high ionic strength and are recovered by washing the resin with an aqueous solution having a low ionic strength.

The process of this invention is also distinguishable from the adsorption-desorption process disclosed in the aforementioned U.S. Pat. No. 4,729,834 in that the adsorption-desorption process is driven by ionic strength rather than temperature. Thus, it is unnecessary to employ a higher temperature for adsorption than for desorption although such a temperature gradient is not foreclosed.

The process has specific application in two reactions. The first is the interfacial condensation polymerization of bisphenols as illustrated by bisphenol A also known as 2,2-bis(4-hydroxyphenyl)propane with phosgene to produce various polycarbonates, wherein amine or amine salts or mixtures thereof which function as phase transfer catalysts in said interfacial process are recycled and re-used by virtue of being recovered through the application of the process of the present invention. The second is the reaction of bisphenol salts such as bisphenol A disodium salt with nitro- or halo-substituted imides such as 4-nitro-N-methylphthalimide, 4-chloro-N-methylphthalimide or 1,3-bis[N-(4-chlorophthalimido)]benzene also known as 2,2'-(1,3-phenylene)bis[5-chloro-1H-isoindole-1,3(2H-dione)], to produce bisimides or polyetherimides.

The preferred adsorbents for use in the process of the instant invention are suspension copolymers of monoethylenically unsaturated monomers and polyvinylidene monomers. The conditions of polymerization, particularly the choice of solvents and precipitating agents, can be so chosen as to produce a copolymer that has a fairly high specific surface area along with a useful microporosity. Such high surface coupled with microporosity leads to a greater accessibility of the adsorption sites, thereby providing a superior adsorbent. Materials with high specific surface areas tend to have surface work functions that provide a driving force for adsorption. Generally the chemical constitution of the surface will affect the types of molecules preferentially adsorbed thereon. This phenomenon then provides the basis for adsorption purification of suitable substrates. The aforementioned copolymers are suitable for the purification of organic phases.

Particularly preferred absorbents are highly crosslinked suspension polymers of aromatic and/or acrylic monomers such as styrene, ethyl acrylate and methyl methacrylate. Crosslinking is typically achieved by the incorporation of divinyl comonomers such as divinylbenzene. It is sometimes preferred to employ a proportion of divinyl comonomer as high as about 70–80 mole percent. Polymers of this general type are available, for example, from Rohm & Haas under the designations "XAD-4" and "XAD-7".

The invention comprises a process wherein an aqueous brine comprising an organic base and containing about 5–40% by weight of dissolved salts as NaCl, i.e. a brine having a high ionic strength, is contacted with a resin as described hereinabove. Other salts, typically nitrites such as sodium nitrite, can replace all or part of the NaCl on a mole-for-mole basis.

A principal feature of the invention is the fact that the high ionic strength of said brine serves as a driving force for adsorption of said organic base on said resin. Further, the use of water during the desorption step as described hereinafter serves as a driving force for desorption of the base from the resin.

Typically, the resin is present in at least one adsorption column through which the brine passes in a downward direction. The organic base is adsorbed onto the resin and the resulting purified brine may now be electrolyzed to generate chlorine or other halogens without the hazardous generation of nitrogen tri-halide compounds, diluted and safely disposed, or recycled as process water or brine with or without any salt make-up that may be necessary.

The organic base is desorbed by washing the adsorbed resin with pure water or a brine having a significantly lower salt content, i.e. a lower ionic strength, than that from which the organic base was adsorbed onto the resin. Washing may be countercurrent but it generally preferably cocurrent to the direction of brine passage during adsorption. The process of washing the resin desorbs the adsorbed organic base and regenerates the resin which may be re-used. Consequently one embodiment of the process is a cyclic process wherein organic base is adsorbed and desorbed by a water wash, which also regenerates the resin for further adsorption-desorption cycles.

Various combinations and permutations of process functions effective for adsorbing organic compounds soluble in brines onto a polymeric resin are included in the present invention. For example, two or more adsorption columns can be used in parallel with appropriate switching valves such that while one column is being operated in an adsorption mode, one or more of the others operates in a desorption and/or regeneration mode. This process configuration would have the advantage of permitting continuous operation without any need to interrupt the flow of organic compound containing brine to the resin containing adsorption column. The choice of which flow scheme would be employed would depend on large part whether or not the interfacial polymerization or other source process generating the organic containing brine is being operated in a batch or continuous mode. In the case of a batch mode, a single adsorption reactor would tend to be preferred from the standpoint of process engineering and economic considerations. In contrast, continuous processes would tend to require a parallel adsorption train that would permit continuous removal of the organic contaminants from the brine.

It will also be appreciated that art-recognized modifications can be made in the process to accommodate the recovery of guanidinium salts from ether imide product streams.

Depending on what types of catalysts are employed in the synthesis reaction, the process of the instant invention will have one of two preferred embodiments. The phase transfer catalysts typically employed in an interfacial or ether imide process are amine salts or guanidinium salts. Since these salts already exist in an ionizable or ionic form, their partition between organic and aqueous phases in the various process streams of the process tends to be a function of the organic solvent or the ionic strength of the aqueous solution and the solute loads in those solutions.

In contrast, when a mixed or binary catalyst system is used, one that utilizes both a quaternary organic ammonium salt as a phase transfer catalyst and an unprotonated tertiary amine as a co-catalyst, it becomes more important to consider the solubility of the tertiary amine component as a function of the hydrogen ion concentration, or pH. At pH values greater than 7, tertiary amines will tend to exist in aqueous solution as the solvated free amine. At pH values ranging from 7 to 14, the highly lipophilic character of organic tertiary amines provides a driving force for adsorption onto the adsorbent resin. Thus the wash water utilized for desorption for the recovery of mixed catalysts adsorbed onto the adsorbent resin should have a pH below about 7, i.e. in the acid range. The acid conditions of the wash water solution protonate the adsorbed tertiary amine, converting it to an ammonium salt and thereby rendering it more soluble in the aqueous phase.

Desorption may be facilitated by increasing the temperature of the desorbing solvent, contrary to the disclosure of the aforementioned U.S. Pat. No. 4,792,834. In the case of water as the desorbing solvent, recovery of quaternary ammonium salt and any adsorbed tertiary amine is increased by increasing the solvent temperature from about 20° to about 90° C.

There are thus two modes of adsorption-desorption to be utilized, depending on the type of catalyst system being used in the synthesis reaction. The first is pH independent, while the second utilizes an acidic aqueous solution to wash or desorb the adsorbed co-catalyst and phase transfer catalysts from the adsorbent resin.

The following examples of a reduction to practice are illustrative of the present invention. All percentages are by weight.

EXAMPLE 1

A column of internal dimensions 25 cm in length and 2.7 cm diameter, possessing a volume of 143.13 cc, was charged with 97 g of "XAD-4", a non-ion-exchangeable adsorbent styrene-divinylbenzene suspension copolymer having a proportion of divinylbenzene units on the order of 70–80 mole percent. The column was partially filled with water and the resin introduced from the top of the column. As the column was filled, water was released from the bottom to prevent overflowing. After filling the column with wet resin, each end of the column was tightly fitted to restrict expansion of the packing material.

A peristaltic pump was then used to pump through the column, at 24° C., a synthetic brine which was a 20% aqueous solution of NaCl doped with 560 wppm methyltributylammonium chloride (MTBA). The brine was pumped through the resin-containing column at a rate of 20 ml/min, which is a space velocity of 8.4 column or bed volumes per hour.

The column eluent was monitored to determine the efficiency and completeness of adsorption. Breakthrough, defined as when 1 wppm of phase transfer catalyst was detected in the eluent, was observed when approximately 6 kg of brine had been passed through the column.

EXAMPLE 2

The procedure of Example 1 was repeated, using a synthetic brine doped with 280 wppm MTBA. Breakthrough was observed after 12 kg of brine had passed through the column.

EXAMPLE 3

The procedure of Example 1 was repeated, using a synthetic brine doped with 112 wppm MTBA. Breakthrough was observed after 28 kg of brine had passed through the column.

EXAMPLE 4

The procedure of Example 1 was repeated, using a synthetic brine having a salt concentration of 13.5%. Breakthrough was observed after 6 kg of the brine had passed through the column.

EXAMPLE 5

The procedure of Example 1 was repeated, except that the synthetic brine was replaced by a reaction brine from the aqueous phase of a commercial interfacial polymerization of bisphenol A, containing NaCl, low levels of phenols, methylene chloride and carbonate salts and doped with 560 wppm MTBA, and the column temperature was 20° C. Approximately 8 kg of brine solution was passed through the column before breakthrough was observed.

EXAMPLE 6

Regeneration of the column used in Example 5 was accomplished by stopping the flow of brine and washing in a countercurrent direction with deionized water. The column was then eluted with a catalyst-free commercial reaction brine containing 1000 wppm methylene chloride (1 g methylene chloride/1000 g brine). After 16 kg of the brine had passed through the column, breakthrough was observed. The adsorption of the methylene chloride caused the column to swell.

A similar brine doped with 560 wppm MTBA was passed through the column and breakthrough was observed at 8 kg of brine.

EXAMPLE 7

Following regeneration of the column used in Example 5, the identical brine was used except that an additional 1000 wppm of triethylamine was added. The pH of this brine solution was about 10.5. After 3.4 kg of this doubly doped brine had passed through the column, breakthrough of the MTBA was observed. Both MTBA and the triethylamine were adsorbed onto the column.

EXAMPLE 8

The procedure of Example 5 was repeated and additional brine was passed through the column and the level of MTBA in the eluent was monitored. The results are listed in the following table.

| Brine, kg | Eluent MTBA level, wppm |
| --- | --- |
| 8 | 1.16 |
| 9 | 3.02 |
| 10 | 11.7 |
| 11 | 13.9 |
| 12 | 79.1 |
| 13 | 143 |
| 14 | 163 |
| 15 | 236 |
| 16 | 395 |
| 17 | 427 |
| 18 | 476 |
| 19 | 459 |
| 20 | 464 |

EXAMPLE 9

The procedure of Example 1 was repeated, except that the column was charged with "XAD-7", a non-ion-exchangeable adsorbent copolymer similar to "XAD-4" but having methyl methacrylate units rather than styrene units, and the synthetic brine had a NaCl concentration of 17.6% and was doped with 480 wppm MTBA. Approximately 2.8 kg of doped brine solution was passed through the column before breakthrough was observed.

EXAMPLE 10

Recovery of MTBA from the XAD-4 resin used in Examples 1–6 was nearly identical in all cases. Pure water was passed through the resin-containing column at 20° C. in a countercurrent direction at a flow of 4 ml/min which is a space velocity of 1.58 ml/hr. No significant levels of MTBA were observed in the first 70 g of water exiting the column during the wash. As the wash water exited the column, the level of MTBA rose quickly to a maximum value of approximately 30,000 wppm. Use of 1,000 g of wash water allowed for recovery of approximately 90% of the MTBA adsorbed onto the column. The level of MTBA in the wash water after 1,000 g of wash water had passed through the column was approximately 1,000 wppm.

Repeating the water wash at 80° C., the peak level of MTBA was observed in the wash water exiting the column is 46,000 wppm. Again, the level of MTBA in the wash water after 1,000 g of wash water had passed through the column was approximately 1000 wppm.

EXAMPLE 11

The desorption procedure of Example 10 was performed on the nearly saturated resin as prepared in Example 9. Peak MTBA concentrations in the wash water varied as a function of wash water temperature. At 20° C. the peak MTBA concentration was 50,000 wppm and at 80° C. it was 141,000 wppm.

EXAMPLE 12

The desorption procedure of Example 10 was repeated, using the resin from Examples 5–6. The MTBA desorbed in a fashion similar to that observed in Example 11 with the exception that the resin shrank as methylene chloride also desorbed.

EXAMPLE 13

Recovery of MTBA from the sorbed resin of Example 9, which contained added triethylamine, using pure wash water appeared to proceed in the same manner as a normal desorption. However, a subsequent adsorption using a brine also containing 560 wppm MTBA failed to treat the expected 8 kg of brine. Pure water washing apparently failed to remove all of the adsorbed triethylamine. Washing with a slightly acidic water solution, pH below about 5.5, did remove the remaining adsorbed triethylamine. At pH's above about 9.5, the free triethylamine did adsorb well onto the resin.

EXAMPLE 14

The resin used in Example 11 was washed with pure water at a flow rate of 2 ml/min, which is a space velocity of 0.79 ml/cc/hr. The peak concentration observed for the MTBA was 11,000 wppm. Essentially all of the adsorbed MTBA was recovered with a 200 ml water wash.

Summarizing Examples 1–14: Examples 1–3 demonstrate dependence of breakthrough on the concentration of quaternary ammonium salt present in the brine, suggesting a fixed adsorption capacity for the resin. Example 4 demonstrates that adsorption of the quaternary ammonium salt onto the resin is independent of salt concentration in the brine. Examples 5–6 show that while other organics such as methylene chloride may adsorb onto the column, the adsorption of the quaternary ammonium salt is not inhibited thereby. Example 7 shows that the addition of other nitrogenous compounds to the brine proportionally reduces the ability of the resin to adsorb the quaternary ammonium salt. Example 8 demonstrates that the resin still retains adsorptive capacity even after breakthrough. Example 9 demonstrates adsorption using an alternative resin. Example 10 demonstrates countercurrent desorption. Example 11 demonstrates an increasing efficiency of desorption with an increasing temperature of the wash water. Example 12 demonstrates that swelling of the resin by adsorption of an organic compound such as methylene chloride does not interfere with desorption. Example 13 demonstrates that recovery of a mixture of amine salts and tertiary amines is facilitated by the use of an acidic water wash desorption. Example 14 demonstrates desorption using the alternative resin.

EXAMPLE 15

A column similar to that of Example 1 and packed with the same resin was employed in the same manner to remove hexaethylguanidinium bromide from a synthetic brine consisting of 914 g water, 247 g sodium nitrite, 9.14 g 50% aqueous sodium hydroxide solution, 9.08 g hexaethylguanidinium bromide and 700 µl toluene. The resin was initially washed with 1 l of deionized water and was then preconditioned with 1 l of 20% aqueous sodium nitrite brine. Synthetic brine, 1 l, was then introduced at 20° C. and 20 ml/min. The process was followed by calorimetric analysis of the effluents at various stages and dilutions, using a methyl orange-boric acid indicator. Breakthrough was observed at 600 ml. Desorption was performed at 20° C. with deionized water.

What is claimed is:

1. A process for the adsorption of catalyst-derived salts selected from the group consisting of tertiary amine, quaternary ammonium and guanidinium salts from an aqueous brine having an ionic strength equivalent to a sodium chloride level of about 5–40% by weight and having therein one or more of said catalyst-derived salts, said brine being selected from the group consisting of:
   brines produced in an interfacial polycarbonate-forming reaction and comprising alkali metal salts resulting from pH control of the reaction and water soluble chloroformate hydrolysis products, and
   brines produced in a displacement reaction between an alkali metal salt of a dihydroxyaromatic compound and a monomeric or polymeric nitro- or halo-substituted aromatic compound and comprising phase transfer catalyst and at least one alkali metal nitrite, chloride or bromide;
   comprising contacting said aqueous brine with a non-ion-exchangeable adsorbent polymeric resin whereby said brine is depleted in the concentration of said catalyst-derived salts by the adsorption thereof onto said resin.

2. The process of claim 1 wherein said catalyst-derived salt is selected from the group consisting of tertiary and quaternary ammonium salts.

3. The process of claim 1 wherein said catalyst-derived salt comprises a guanidinium salt.

4. The process of claim 1 wherein said resin is a suspension polymer of an aromatic or acrylic monomer with a divinyl comonomer, said divinyl comonomer being employed in a proportion of about 70–80 mole percent.

5. A process for adsorption and desorption of catalyst-derived salts selected from the group consisting of tertiary amine, quaternary ammonium and guanidinium salts, comprising:
   adsorbing said catalyst-derived salts from an aqueous brine having an ionic strength equivalent to a sodium chloride level of about 5–40% by weight and having therein one or more of said salts, said brine being selected from the group consisting of:
   brines produced in an interfacial polycarbonate-forming reaction and comprising alkali metal salts resulting from pH control of the reaction and water soluble chloroformate hydrolysis products, and
   brines produced in a displacement reaction between an alkali metal salt of a dihydroxyaromatic compound and a monomeric or polymeric nitro- or halo-substituted aromatic compound and comprising phase transfer catalyst and at least one alkali metal nitrite, chloride or bromide;
   by contact of said aqueous brine with a non-ion-exchangeable adsorbent polymeric resin whereby said brine is depleted in the concentration of said catalyst-derived salts by the adsorption thereof onto said resin; and desorbing said catalyst-derived salts by washing said resin with an amount of a solvent effective to remove said catalyst-derived salts therefrom, whereby said catalyst-derived salts are dissolved in said solvent.

6. The process of claim 5 wherein the solvent is water.

7. The process of claim 6 wherein said catalyst-derived salts are selected from the group consisting of tertiary and quaternary ammonium salts.

8. The process of claim 6 wherein said catalyst-derived salts comprise a guanidinium salt.

9. The process of claim 6 wherein said resin is a suspension polymer of an aromatic or acrylic monomer with a divinyl comonomer, said divinyl comonomer being employed in a proportion of about 70–80 mole percent.

* * * * *